United States Patent [19]
Nelson et al.

[11] Patent Number: 5,649,974
[45] Date of Patent: Jul. 22, 1997

[54] LOW PROFILE DEFIBRILLATION CATHETER

[75] Inventors: Randall S. Nelson, Pine Springs; Mark W. Kroll, Minnetonka, both of Minn.

[73] Assignee: Angeion Corporation, Plymouth, Minn.

[21] Appl. No.: 520,533

[22] Filed: Aug. 28, 1995

Related U.S. Application Data

[63] Continuation-in-part of Ser. No. 298,213, Aug. 29, 1994, abandoned, which is a continuation-in-part of Ser. No. 919,233, Jul. 27, 1992, Pat. No. 5,454,839.

[51] Int. Cl.$^6$ ..................................................... A61N 1/05
[52] U.S. Cl. ................................................. 607/122; 29/825
[58] Field of Search ........................................ 607/122, 123, 607/119, 5, 4; 128/642; 29/857, 825

[56] References Cited

U.S. PATENT DOCUMENTS

| | | |
|---|---|---|
| 3,614,954 | 10/1971 | Mirowski et al. . |
| 3,769,984 | 11/1973 | Muench .................. 607/122 |
| 3,942,536 | 3/1976 | Mirowski et al. . |
| 4,161,952 | 7/1979 | Kinney et al. ............ 607/122 |
| 4,355,646 | 10/1982 | Kallok et al. . |
| 4,481,953 | 11/1984 | Gold ........................ 607/122 |
| 4,499,907 | 2/1985 | Kallok et al. ............ 607/122 |
| 4,603,705 | 8/1986 | Speicher et al. ......... 607/122 |
| 4,640,983 | 2/1987 | Comte . |
| 4,718,423 | 1/1988 | Willis et al. . |
| 4,922,927 | 5/1990 | Fine et al. . |
| 4,932,407 | 6/1990 | Williams . |
| 4,974,588 | 12/1990 | Smits . |
| 5,007,436 | 4/1991 | Smits . |
| 5,115,818 | 5/1992 | Holleman et al. . |
| 5,165,403 | 11/1992 | Mehra . |
| 5,257,634 | 11/1993 | Kroll . |
| 5,265,623 | 11/1993 | Kroll et al. . |
| 5,269,319 | 12/1993 | Schulte et al. ........... 607/123 |

FOREIGN PATENT DOCUMENTS

| | | |
|---|---|---|
| 0491979 | 7/1992 | European Pat. Off. . |
| 2009329 | 6/1992 | WIPO . |

*Primary Examiner*—William E. Kamm
*Assistant Examiner*—Kennedy J. Schaetzle
*Attorney, Agent, or Firm*—Brad D. Pedersen

[57] ABSTRACT

A low profile defibrillation catheter is disclosed which is much thinner than existing devices. The thin structure is provided by using the current conductor coil as a first electrode coil and the same materials as the conductor for the second electrode. The second electrode coil is bonded to the second conductor coil and wound in the same direction. The thin design is motivated by an electrical field analysis which reveals that the length of the catheter is the important determinant of defibrillation efficacy, and that the large radius and surface area of prior art devices were less beneficial.

27 Claims, 7 Drawing Sheets

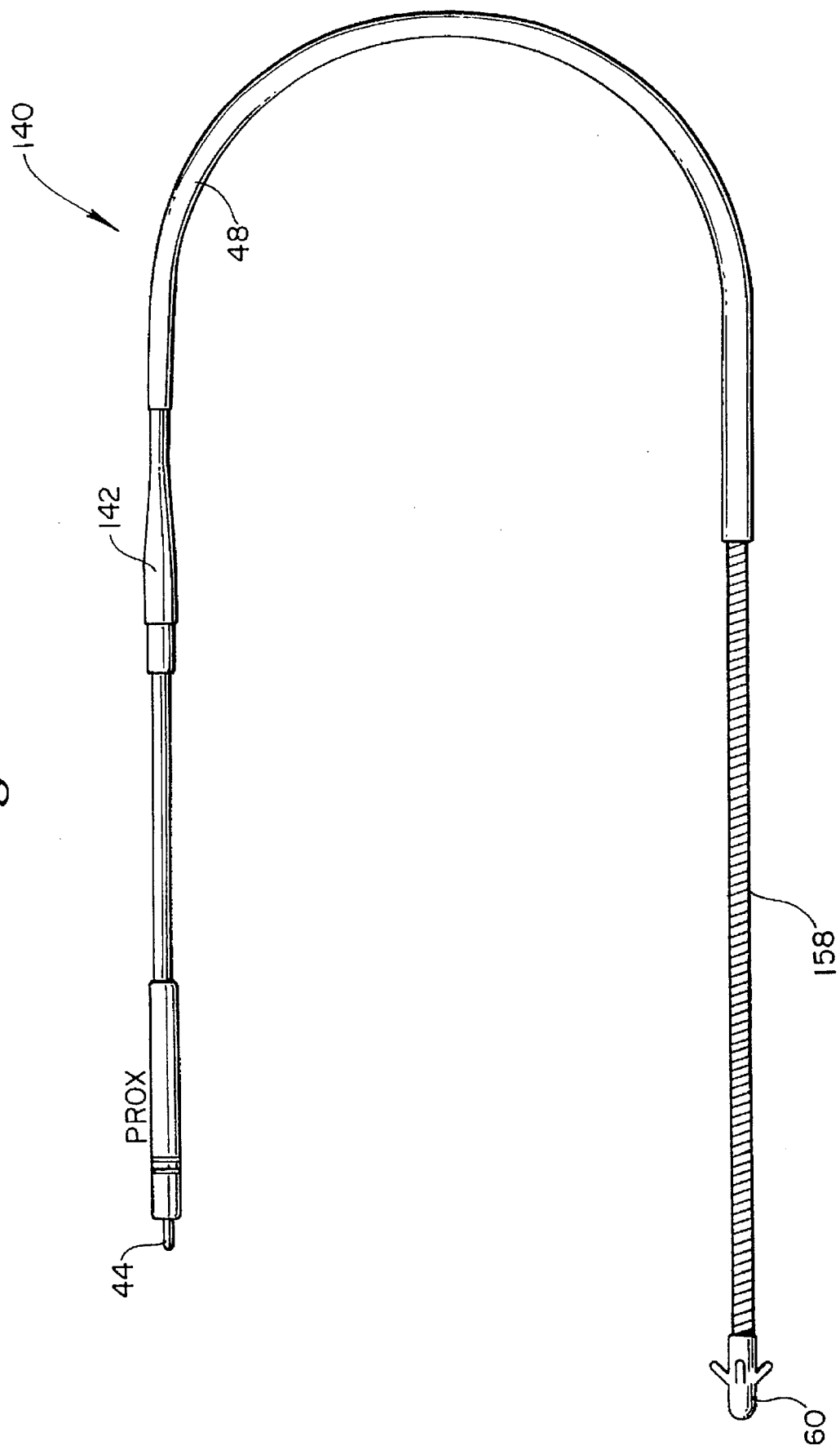

LOW PROFILE DEFIBRILLATION CATHETER

CROSS REFERENCES TO APPLICATION

This application is a continuation-in-part application of Ser. No. 08/298,213, filed Aug. 29, 1994, now abandoned, which is a continuation-in-part of an application Ser. No. 07/919,233, filed Jul. 27, 1992, now issued as U.S. Pat. No. 5,454,839.

FIELD OF THE INVENTION

The present invention pertains to a defibrillation device and, more particularly, refers to a low profile defibrillation catheter where at least one of the current conductors is utilized as a defibrillation electrode.

BACKGROUND OF THE INVENTION

The implantable defibrillator requires the use of electrodes to conduct large currents through the human heart. Previously, these electrodes have typically been two or more patches stitched to the heart. These are referred to as epicardial-patch electrodes and require the surgeon to open the chest cavity for placement.

To avoid the surgery required for the epicardial patches, electrode coils are sometimes inserted into the heart chambers via venous routes using various procedures known within the medical and surgical arts. In practice, a vein such as the right or left cephalic vein or the internal or external jugular vein is selected for insertion. The selected vein is exposed by a standard surgical cutdown procedure. The tapered end of a vein pick is inserted into the incised, selected vein. An introducer is then pushed underneath the vein pick into the vein. The defibrillation catheter is then slid into the introducer and the introducer, with the inserted catheter lead, is then gently fed into the vein. The introducer is then peeled away and discarded. Usually using fluoroscopy, the catheter is then gently pushed through the vein into the vena cava and thence into the heart, where it is positioned.

Defibrillation coils, used to deliver the electrical current to defibrillate the heart muscle, are often mounted or integral with other functional elements in defibrillation catheters. These coils are known as transvenous electrodes. One coil generally sits just above the right atrium (RA) in a location within the superior vena cava right (SVC). The other coil generally lies within the right ventricle at the right ventricular apex (RVA).

Unfortunately, catheter electrodes are often unable to direct sufficient current through enough of the heart muscle to effect defibrillation. For this reason, a small patch is often inserted just under the skin on the patient's left side, thus requiring additional, but minimal, surgery. This "subcutaneous patch" is not in direct contact with the heart, but provides for a current vector between the transvenous electrode to the subcutaneous patch, thereby passing through the heart muscle. Thus, the subcutaneous patch assists in directing current through the heart muscle, and hence, facilitates defibrillating the heart.

There are two primary electrical requirements for defibrillation electrodes. The first is that the resistance be low enough to allow the passage of a large current through the heart. The second requirement is that the current vector passes through the vast majority of the heart muscle. This second requirement is usually met by having sufficient extent to the electrodes and by careful positioning. Thus, other than placement, the primary barrier to increased utilization of catheter electrodes for defibrillation relates to the ability to successfully lower electrode resistances.

U.S. Pat. No. 5,265,623 issued to Kroll et al. attempted to more evenly distribute the electrical energy emitted by the claimed electrode during defibrillation by positioning the electrode-conductor connection at or near the mid-point of the electrode. Seeking better defibrillation efficacy by this design, Kroll et al. failed to realize the relative importance of relative electrode dimensions in reducing electrode resistances, other than stating that electrodes with smaller radii generated greater electrical fields. Kroll et al. also taught a preference for electrode lengths of less than 30 times the diameter of the electrode. While Kroll et al. represented an advance in defibrillating catheter technology, the importance of catheter electrode dimensions was neither known nor taught.

Another advance in this field was represented by the teachings of U.S. Pat. No. 5,257,634, issued to Kroll. Kroll correctly taught the importance of increased electrode length, but totally failed to address the lesser, but nonetheless substantial importance of catheter diameter. Kroll taught the construction and use of defibrillation electrodes that maximized the effective length of the electrode by employing flexible resilient extension members to the electrode body. While the electrodes of Kroll represented another advance in defibrillator cathode technology, the main purpose was to achieve the maximum possible effective electrode length without the appreciation of some optimum levels or ratios of catheter length and diameter design dimensions.

Detailed herein are new physical embodiments of cardioversion defibrillation transvenous catheters with lower electrode resistances. These improved catheters have been enabled by a theoretical discovery which nullifies previous assumptions that maximized electrode surface area or electrode diameter as the most efficient means of constructing catheters with minimum electrode resistances.

SUMMARY OF THE INVENTION

The present invention is a cardioversion defibrillation transvenous catheter having at least two electrode coils, each electrode coil having a maximum diameter of less than about 6 French. The electrode coils are longitudinally positioned and coaxial with each other in the catheter. The first electrode coil surrounds the second electrode coil for a portion of the catheter length where both the first and second electrode coils are within a dielectric material and terminates at a first electrode coil not having a dielectric material surrounding the first electrode coil. The second electrode conductor extends beyond the first electrode coil where the second electrode conductor is within the dielectric material and terminates at the distal end of the catheter, where it is bonded to the second electrode coil.

The cardioversion defibrillation transvenous catheter has an exposed length of at least one of the at least two electrode coils which is over 30 times, and preferably over 35 times, the maximum catheter electrode diameter.

The cardioversion defibrillation transvenous catheter has an exposed length of at least one of the at least two electrode coils which runs along substantially all of the entire inner distance of an average adult human right ventricle, from the right ventricular apex to the entrance of the right ventricle at the coronary tricuspid valve.

Alternatively, the catheter of the present invention may have a single electrode coil, the electrode coil having a maximum diameter of less than about 6 French. The single electrode has an exposed length of the electrode coil which is over 30 times, and preferably over 35 times, the maximum catheter electrode diameter. The cardioversion defibrillation transvenous catheter may have an exposed length of electrode coil which runs along substantially all of the entire inner distance of an average adult human right ventricle, from the right ventricular apex to the entrance of the right ventricle at the tricuspid valve.

BRIEF DESCRIPTION OF THE DRAWINGS

FIG. 10 illustrates a plan view of a single electrode embodiment of the low profile defibrillation catheter according to the present invention.

DETAILED DESCRIPTION OF THE INVENTION

Figure 1:
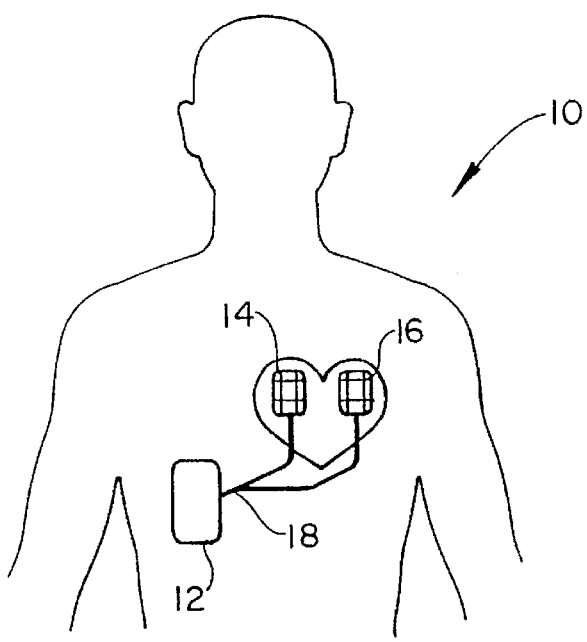
FIG. 1 illustrates a schematic representation of a defibrillating system of the prior art implanted in the abdominal cavity, with epicardial-patch electrodes attached directly to the heart.

Other objects of the present invention and many of the attendant advantages of the present invention will be readily appreciated as the same becomes better understood by reference to the following detailed description when considered in connection with the accompanying drawings, in which like reference numerals designate like parts throughout the figures.

FIG. 1 illustrates a schematic drawing of a patient 10 fitted with a defibrillating system of prior art consisting of a pulse generator 12 implanted in the abdominal cavity and connected to epicardial-patch electrodes 14 and 16 by electrical-lead harness 18. The placement of epicardial-patch electrodes onto the surface of the heart requires that the surgeon open the chest cavity for placement. This is a much more risky procedure than the procedure required to emplace the present invention. Furthermore, patients in need of defibrillating catheters often are poor candidates for surgical procedures requiring that the chest cavity be opened, thereby precluding them from obtaining the life saving benefits that could otherwise result from inventions of the prior art.

Figure 2:
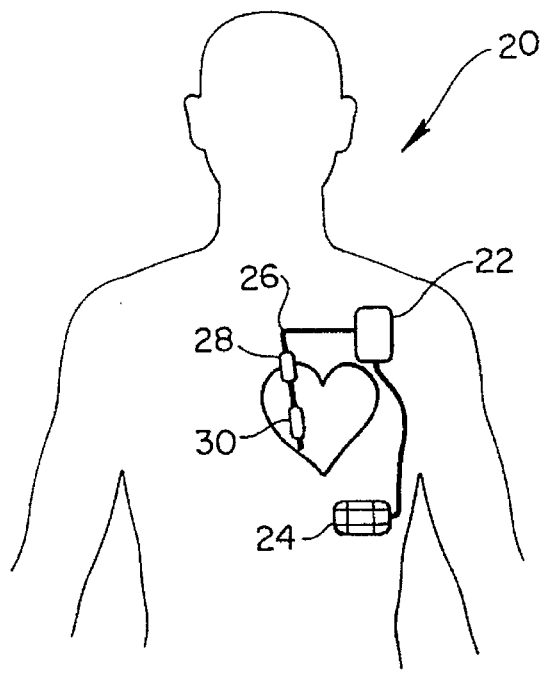
FIG. 2 illustrates a schematic representation of a defibrillating system of the present invention having a SVC electrode, a RVA electrode and one subcutaneouspatch electrode.

FIG. 2 illustrates a schematic drawing of a patient 20 implanted with a defibrillating system of the present invention, including a subcutaneously implanted pulse generator 22 in a subclavian position, a subcutaneous patch electrode 24, and a transvenous catheter 26, carrying a SVC electrode coil 28, and a RVA electrode coil 30. To avoid the surgery required for epicardial patches 14 and 16 of FIG. 1, electrode coils 28 and 30 are passed transvenously into the heart chambers usually following the subclavian vein to the superior vena cava and into the heart. Electrode coil 28 sits just above the right heart in the superior vena cava at or near its entrance to the right atrium, and coil electrode 30 lies in the right ventricular apex.

The means by which a coronary fibrillation is detected are known within the art. Often housed within the pulse generator, the electrical and mechanical sensing equipment detects a coronary fibrillation event. In response to detecting the fibrillation event, the pulse generator sends an electrical pulse to either the SCV electrode coil, the RVA electrode coil, or both. Unfortunately, catheter-borne electrodes are often unable to direct sufficient current through enough of the heart muscle to effect defibrillation. For this reason, as depicted in FIG. 2, a small subcutaneous patch electrode 24 is inserted just under the skin, on the patient's left side. This requires additional, but minimal, surgery. This "subcutaneous patch" is not in direct contact with the heart, but enables a current vector starting at a transvenous electrode to pass through the heart muscle. Thus, subcutaneous patch electrode 24 assists in directing current through the heart muscle, and hence, in defibrillating the heart. The electrode coil (or coils) receiving the electrical pulse then emit the pulse which passes to the subcutaneous patch electrode. A vector of electrical current is thereby established. The vector of electrical current encompasses all or substantially all of the heart and thereby defibrillates the heart. Alternatively, the emitted electrical pulse can pass to the exterior of the pulse generator, which can be designed to act as an electrode. Or the emitted electrical pulse can pass to both the subcutaneous patch and the exterior of the pulse generator.

There are two primary electrical requirements for defibrillation electrodes. The first is that the resistance be low enough to provide passage of a sufficiently large current through the heart muscle. The second requirement is that the current field lines pass through the vast majority of the heart muscle. This requirement is usually met by having electrodes of sufficient extent. Thus, the primary opportunity for optimization is in lowering the electrode resistance.

Figure 3:
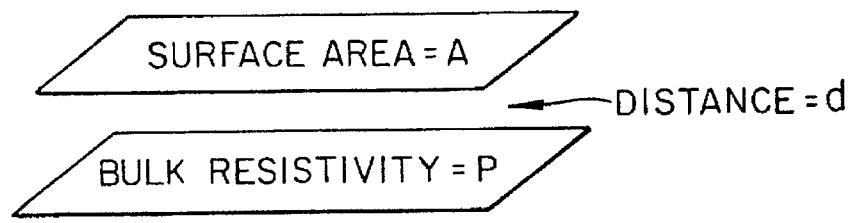
FIG. 3 illustrates a model for estimation of epicardial patch electrode resistance.

The resistance for epicardial patch electrodes can be estimated by using standard formulas from physics and the dimensions of the epicardial patches. As depicted in FIG. 3, the impedance, Z, between two electrodes having surface area, A; separated by distance, d; and having bulk resistivity, p is given by:

$$Z = pd/A \qquad \text{Eq. 1}$$

and thus, a larger surface area is influential for achieving a low impedance. The prior art has sometimes taught surface area alone as being important to enable effective delivery of defibrillation pulses. For example, see U.S. Pat. No. 5,269,319 (Schulte et al.), U.S. Pat. No. 4,603,705 (Speicher et al.) and U.S. Pat. No. 4,481,953 (Gold et al.). Typical values for epicardial patch electrodes are A=30 cm$^2$, d=7 cm and p=150Ωcm. Thus, a typical impedance for epicardial patches across the heart is:

$$Z = \frac{150 * 7}{30} = 35 \, \Omega \qquad \text{Eq. 2}$$

which is a value seen in human implants.

When transvenous catheter electrodes were developed it was assumed that a large radius decreased the gap d between the internal catheter borne electrode, and the patch outside the heart. At the same time, a large radius increased the surface area by $2\pi rl$, where r is radius and l is length. Thus, designs used diameters that were as large as could be forced into the heart through the often narrow veins. Researchers reported their results with catheter defibrillation using large radius electrodes, typically having a radius of 2 mm and a length of 5 cm.

Figure 4:
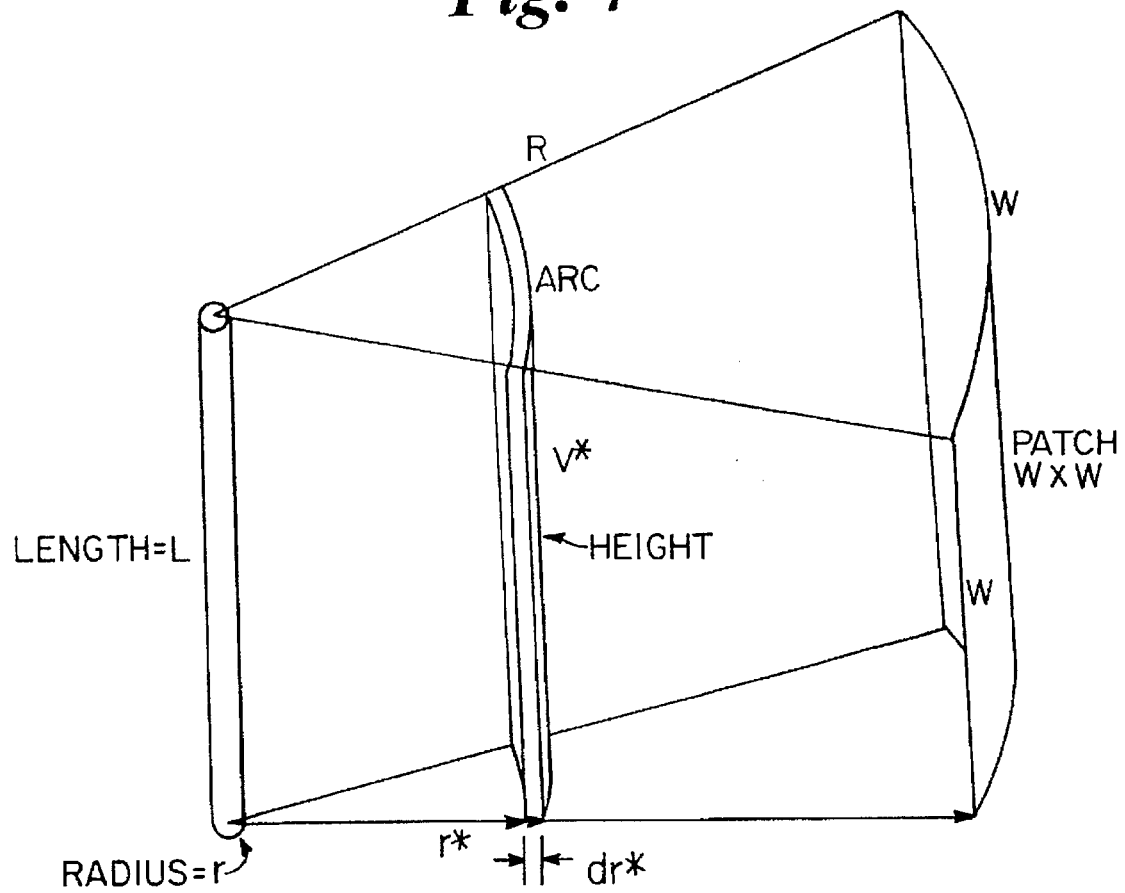
FIG. 4 illustrates a model for estimation of electrical resistance with respect to a cylindrical shell.

A close inspection of the situation for a defibrillation catheter implanted in the right ventricle demonstrates that the impedance model of spaced plates in a fluid is inaccurate. A better mode is depicted in FIG. 4, which depicts a catheter electrode of radius, r; length, L; and spaced a distance, R, from a patch electrode, W×W. Between L and the patch W×W is an infinitesimal volume, V*, with a yet to be determined impedance dZ which can be summed to give an overall impedance Z.

This volume V* is situated in a general, but moveable distance r* from the center of the rod and has an infinitesimal thickness (that is, "gap") dr*. Careful inspection shows that the arc length would be r*W/R and the height L+r*(W−L)/R and multiplied together would be the "area" referred to in Eq. 1. So multiplying resistivity p by gap dr*, dividing by "area", and summing (integrating) the infinitesimal volume from r to R, yields:

$$Z = \int_r^R \frac{p}{\frac{W}{r^*R}\left(\frac{W-L}{(L+Rr^*)}\right)} dr^* = \frac{pR}{WL} \ln\left[\frac{1+Br}{1+BR} \cdot \frac{R}{r}\right] \quad \text{Eq. 3}$$

$$\text{Where } B = \frac{W-L}{RL}$$

Substituting typical values into the product Br shows that Br is small, in the range of −0.01 to +0.01, making the numerator in the ln function essentially 1. Using 1 instead of 1+Br, the above equation simplifies to:

$$Z = \frac{pR}{WL} \ln\frac{(R-L)}{(rW)} \quad \text{Eq. 4}$$

Substituting typical values into Eq. 4 yields an overall impedance of approximately 100 ohms, which is larger than epicardial patches, but a number very close to that found in clinical tests of transvenous leads.

Upon more rigorous inspection, Eq. 4, reveals that impedance is inversely proportional to L and proportional to the natural logarithm of 1/r. The inverse proportionality to L is what conventional thinking suggests in Eq. 3, but ln 1/r entirely changes the situation. Note that the slope of ln(x) is 1/x, meaning that for a large x, the sensitivity to x (that is, the slope of x) has a weak dependance on x when x is large. In the instant case, x=(RL/rW) is indeed large, approximately 50 (R=10 cm; L=8; r=0.2; W=8).

The sensitivity to r can be better shown by looking at the percentage change in Z, dZ/Z, as a function of percentage change in r, dr/r. Mathematically, this is done by taking the differential of Eq. 4 and dividing by Z. One finds:

$$\frac{dZ}{Z} = -\ln\frac{(RL)}{(rw)} - 1 \frac{dr}{r} \quad \text{Eq. 5}$$

Substituting typical values of R=10, L=8, r=0.2 and W=8, one gets dZ/Z=−0.16dr/r. The −0.16 factor is very enlightening. It means that a 1% increase in r will decrease impedance only 0.16%, as opposed to L which, because L is inversely proportional to impedance (see Eq. 4) a 1% increase in L would cause a full 1% decrease in impedance. Thus, there results a greater impedance benefit, with the same $2\pi rL$ area, for making L as long as possible and r as thin as possible.

The more careful analysis done here shows that increasing either L or r will decrease impedance, but that L has a much stronger effect on impedance than does r and, therefore, a long, thin electrode is preferable to a short, thick electrode. In the present invention, the catheter electrode preferably has a maximum diameter of less than about 6 French (i.e., a maximum diameter <2 mm) and an overall length of at least 30 times, and preferably at least 35 times, the maximum diameter of the catheter electrode for a multiple electrode configuration. For a single electrode configuration, the maximum diameter of the electrode is less than about 6 French and preferably less than about 4 French and the overall length of the electrode is at least 30 times, and preferably at least 35 times, the radius of the maximum diameter of the catheter electrode.

FIGS. 5, 6, 7 and 8 illustrate the details of the construction of the catheter. Note that conductor coil 58 is wound continuously to the end of the catheter and is then bonded to the electrode coil 158. This is accomplished by mechanical crimping or laser welding or resistance welding, preferably mechanically crimping and laser welding the conductor coil 58 to either pin 112 or tube 122, then mechanically crimping or laser welding or resistance welding, preferably mechanically crimping and laser welding pin 112 or tube 122 to electrode coil 158.

Figure 5:
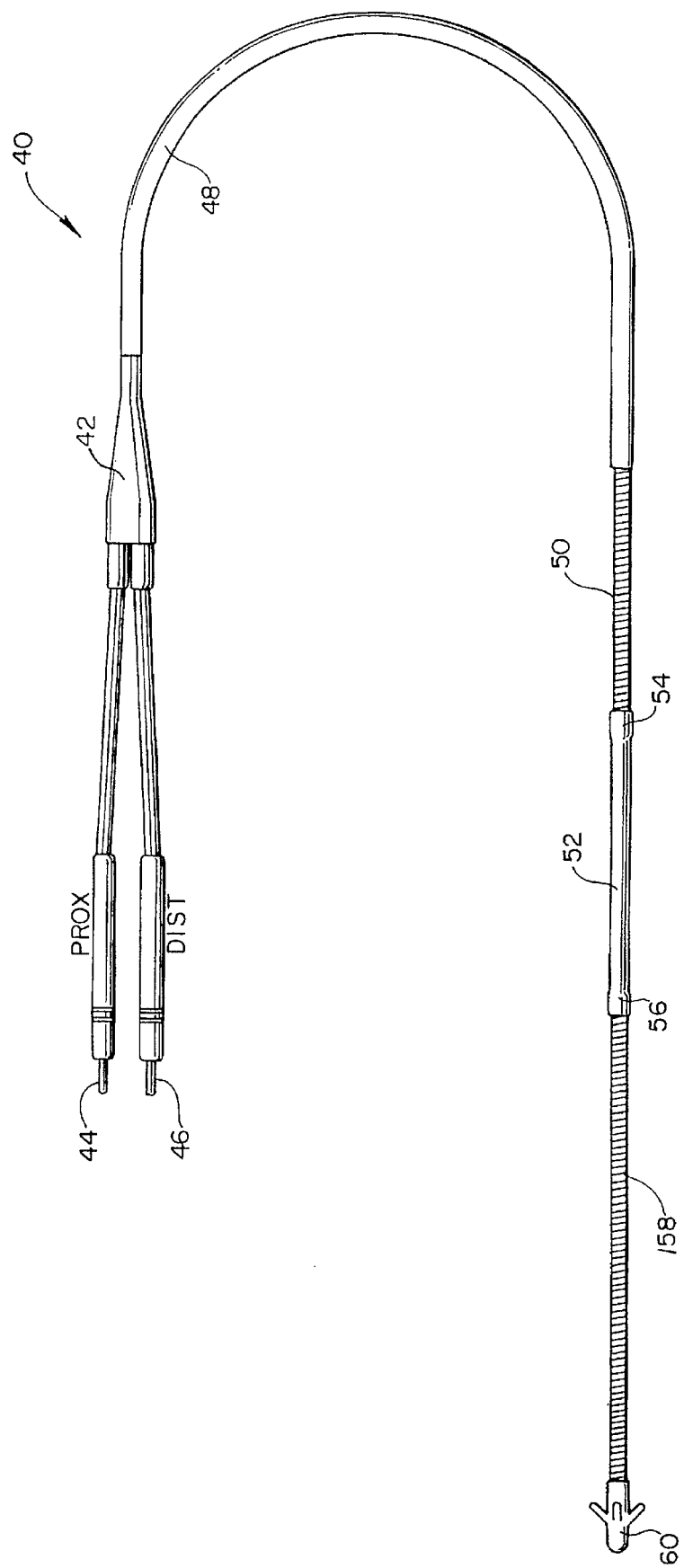
FIG. 5 illustrates a plan view of a low profile defibrillation catheter according to the present invention.

FIG. 5 depicts a plan view of visible members of the low profile defibrillation catheter 40 including a junction member 42, electrical connectors 44 and 46 extending from the proximal end of junction member 42, a dielectric, flexible plastic tubular member 48 extending from the distal end of junction member 42, a flexible wound electrode coil member 50 extending from the interior of flexible plastic tubular member 48, a flexible dielectric plastic tubular covering 52 having flared ends 54 and 56, of which flared end 54 accommodates the distal end of flexible wound coil electrode member 50, flexible wound electrode coil member 158 extending from the interior of flared end 56 and terminating within tined metal catheter tip 60 at the distal end of flexible wound electrode coil member 158. Connector 44 is electrically connected to flexible wound electrode coil member 50 and connector 46 is electrically connected to flexible wound electrode coil member 158. Flexible wound electrode coil member 50 and conductor coil 58 align coaxially within flexible tubular member 48 and than within flared end member 54 as depicted in FIG. 6.

Figure 6:
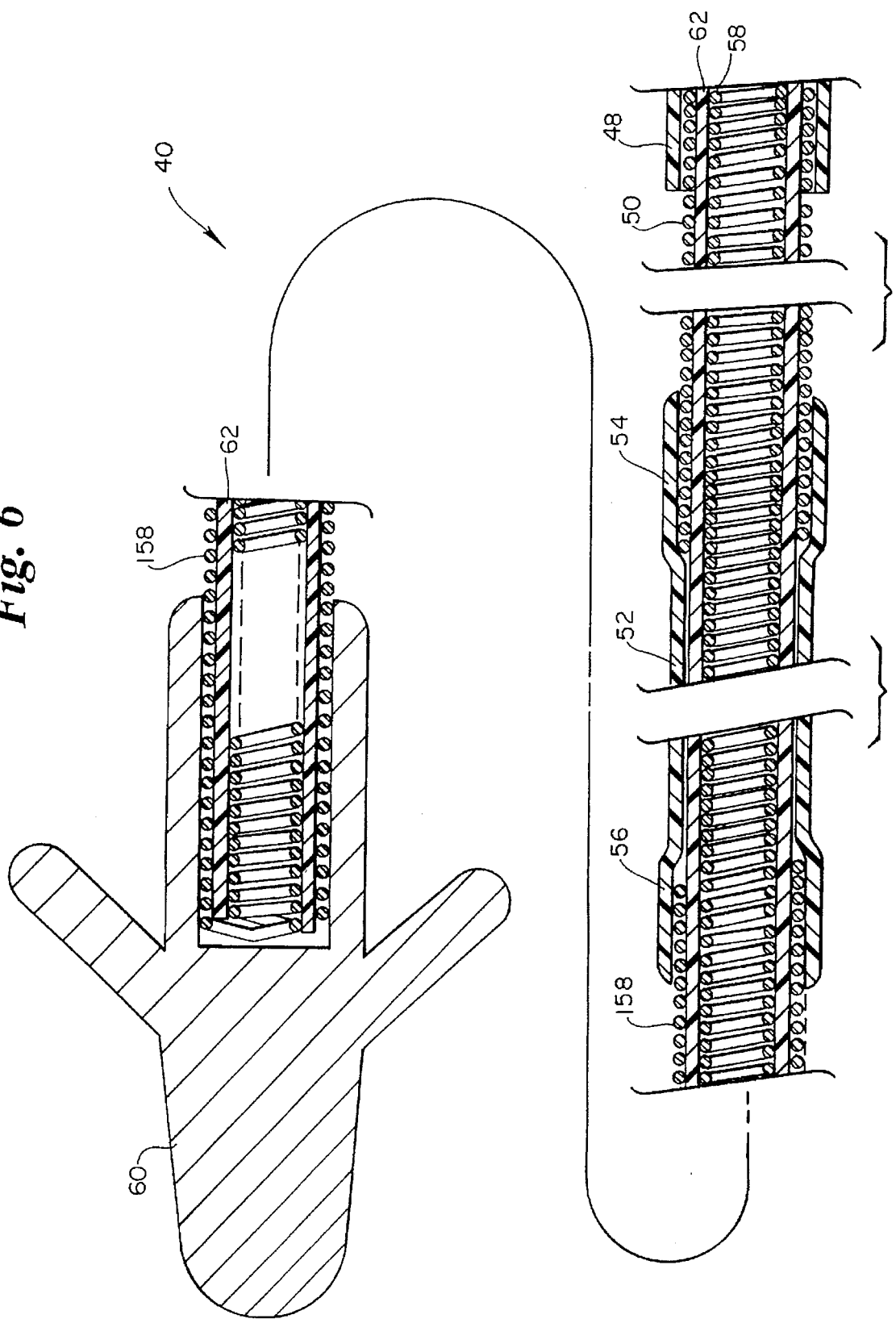
FIG. 6 illustrates a cross-sectional view of a low profile defibrillation catheter according to the present invention.

FIG. 6 depicts a cross-sectional view of the major elements of low profile defibrillation catheter 40. Flexible wound electrode coil 50, flexible plastic tube 62 and flexible wound conductor coil member 58 are arranged in a coaxial fashion within flexible tubular member 48 and continue past the distal end of flexible tubular member 48 to expose flexible wound electrode coil member 50 whose distal end secures and terminates suitably within the confines of flared end 54 of flexible plastic tubular member 52.

Flexible wound conductor coil member 58 resides coaxially within flexible plastic tube 62. Flexible plastic tube 62, in turn, coaxially resides within flexible electrode coil member 158, flexible tubular member 52, or flexible wound electrode coil 50. Flexible wound conductor coil member 58 continues distally, terminating at tined metal catheter tip 60 where it is electrically bonded to flexible wound electrode coil member 158. Flexible wound electrode coil member 158 is appropriately terminated between flexible plastic tube 62 and flare 56 of flexible plastic tubular member 52. As depicted in FIG. 5, the exposure length of exposed electrode coil wires 50 and 158 is extensive along the length of low profile defibrillation catheter 40.

Figure 7:
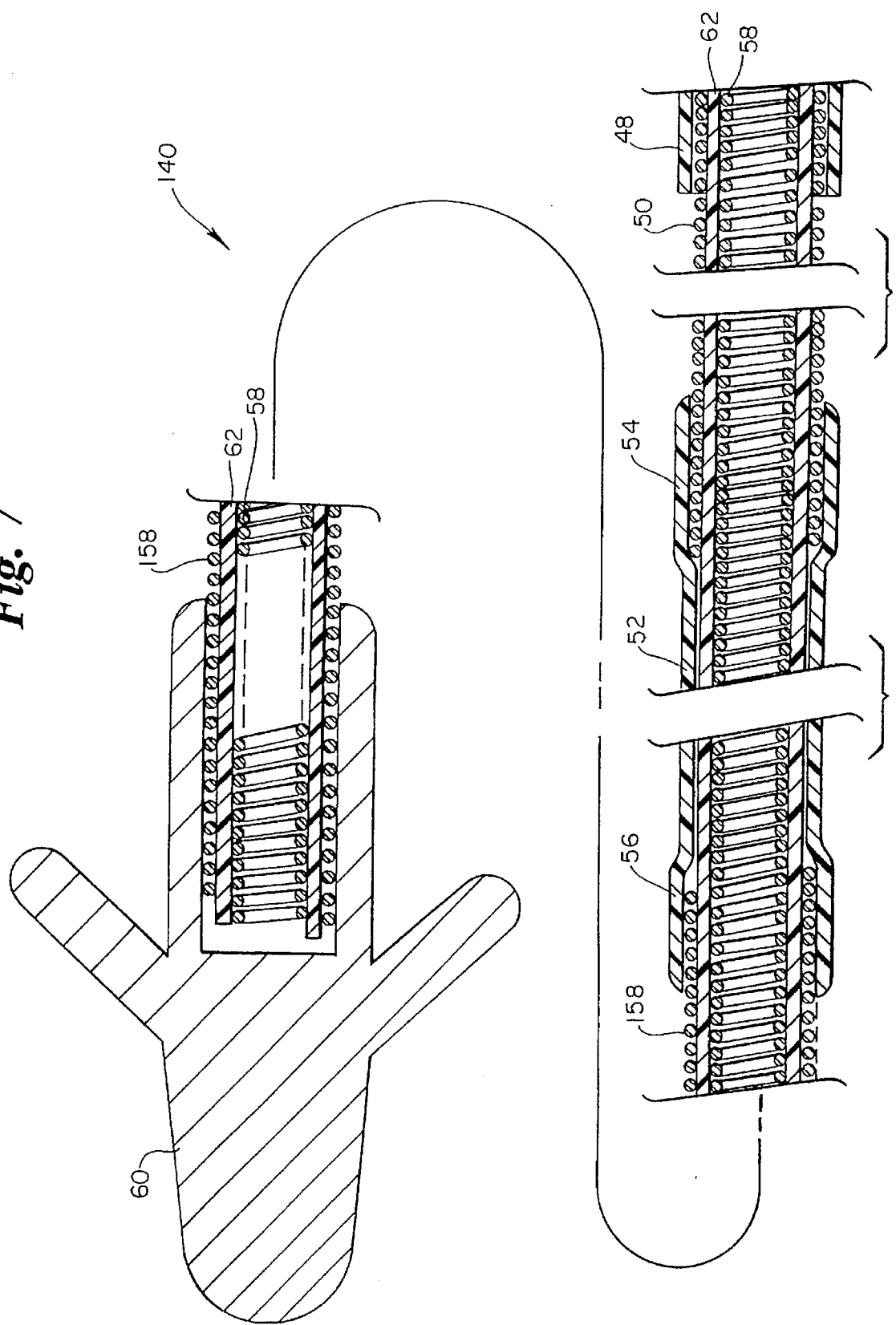
FIG. 7 illustrates a cutaway view of the distal portion of a low profile defibrillation catheter tip showing the attachment of the conductor coil to the electrode coil.
Figure 8:
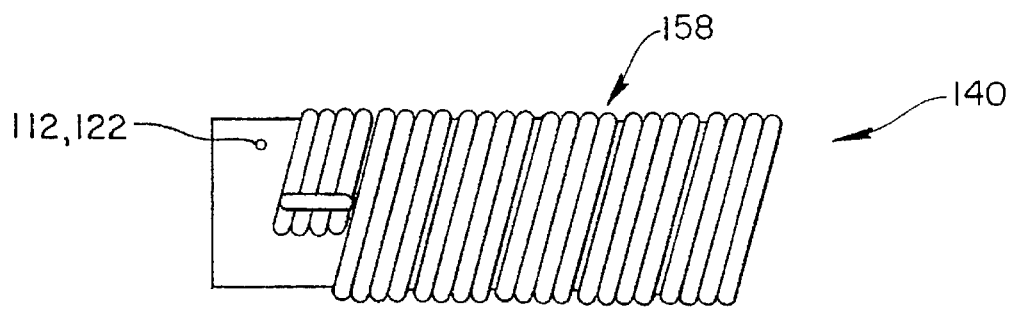
FIG. 8 illustrates a cutaway view of the distal portion of a low profile defibrillation catheter tip showing the attachment between the conductor coil and electrode coil.
Figure 9:
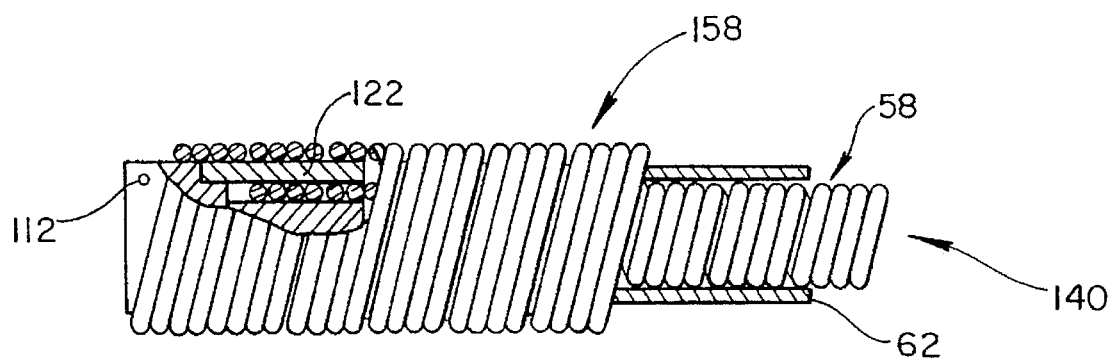
FIG. 9 illustrates a cutaway view of the distal portion of a low profile defibrillation catheter tip showing the winding direction of the conductor coil and electrode coil.

FIG. 7 illustrates a cutaway view of the distal tip portion of low profile defibrillation catheter 40 showing the attachment of conductor coil 58 to electrode coil 158 at the distal end of catheter 40. The distal connection consists of conductor coil 58 (shown in FIG. 8), electrode coil 158 and two machined pieces, pin 112 and tube 122, joined by laser welding, resistance welding, crimping, or a combination of these processes. Conductor coil 58 consists of a coiled multifilar wire, commencing at the proximal end of the lead and terminating at the distal end. It provides a durable, conductive path from the pulse generator to the distal, right ventricular electrode. Electrode coil 158 consists of a coiled unifilar or multifilar wire, round or flat, in cross section, commencing at the distal end of the lead and extending proximally for the designated length of the exposed electrode. One machined pin 112 is inserted into the distal end of the conductor coil and provides a positive stop for the stylet used for implantation as well as a stop for a crimp joint. The second machined piece is a thin walled tube placed over conductor coil 58. The assembly, conductor coil 58, pin 112 and tube 122 is then crimped. As an alternative, tube 122 may be welded onto conductor coil 58. Tube 122 is then welded to pin 112. To finish the electrical connection, electrode coil 158 is then welded, laser or resistance, to tube 122 or pin 112. Alternate constructions for the weld include: (1) welding conductor coil 58 and electrode coil 158 to the surface of pin 112 or tube 122 or (2) welding conductor coil 58 and electrode coil 158 to the end of the pin 112.

The conductor and electrode coil may be constructed from any material used for the purpose including platinum-iridium wire, silver cored MP35N™ wire, or noble metal coated MP35N™ wire (with a silver core). Pin 112 and tube 122 are of the same material which may be MP35N™, titanium, or stainless steel. MP35N™ is an alloy comprising nickel, cobalt, chromium and molybdenum and manufactured by Maryland Specialty Wire Company of Cockeysville, Md. This assembly provides a physical and electrical connection that maintains the same diameter as the electrode (i.e. isodiametric), thereby allowing a low profile distal tip of the lead, which aids in insertion of the lead into a vein during implantation. It also allows the conductor coil and the electrode coil to be wound in the same direction (FIG. 8), thereby eliminating a source of abrasion to flexible plastic tube 62, the insulative material between the two coils. It also provides a stop for a stylet when placed for introduction of the lead into a vein during implantation.

FIG. 10 illustrates a plan view of a single electrode embodiment of the low profile defibrillation catheter 140 according to the present invention. In this single electrode embodiment, junction member 142 is not bifurcated, connecting electrical connector 44, the only electrical connector necessary, to conductor coil 58. Conductor coil 58 extends from the distal end of junction member 142 terminating within the cavity of tined metal catheter tip 60 as previously described. Conductor coil 58 resides coaxially within flexible plastic tube 62 the entire length of the catheter. Flexible plastic tube 62 resides coaxially within electrode coil 158. Electrode coil 158 is electrically bonded to conductor coil 58 in the same fashion as depicted and described in the two electrode embodiment of the present invention described above. Electrode coil 158 extends proximally from tined metal catheter tip 60 along a substantial portion of catheter 140 terminating in the distal end of flexible tubular member 48. The distal end of tubular member 48 may also possess a flared end to better provide for securing electrode coil between tubular member 48 and flexible plastic tube 62. The materials used in this single electrode embodiment are identical to those used and described above with respect to the two electrode embodiment with the exception of junction member 142.

Changes and modifications in the specifically described embodiments can be carried out without departing from the scope of the invention which is intended to be limited only by the scope of the claims thereof.

We claim:

1. A low profile defibrillation catheter comprising:
   a catheter having a proximal end, a distal end and at least one defibrillation electrode located on an exterior surface of the catheter between the proximal end and the distal end and electrically connected to an electrical connector on the proximal end, the defibrillation electrode being electrically bonded to an underlying, insulated conductor coil electrically connected to the electrical connector at the proximal end, and wherein the electrode coil and the conductor coil are wound in the same direction.

2. The defibrillation catheter of claim 1 wherein the catheter includes two defibrillation electrodes, each defibrillation electrode being an electrode coil having a maximum diameter of less than 6 French.

3. The defibrillation catheter of claim 1 wherein the maximum diameter is less than 6 French.

4. The defibrillation catheter of claim 1 wherein the defibrillation electrode has a longitudinal length that is more than thirty times the maximum diameter.

5. The defibrillation catheter of claim 1 wherein the electrode coil and the conductor coil are mechanically and electrically bonded together at a distal end of each.

6. The defibrillation catheter of claim 5 further comprising a cylindrical metallic element coaxial with the distal end of the electrode coil and the conductor coil to which the electrode coil and the conductor coil are mechanically and electrically bonded.

7. A multiple electrode defibrillation catheter comprising:
   a catheter having a proximal end, a distal end and a conductor coil extending longitudinally therebetween, the conductor coil electrically connected to a first electrical connector located at the proximal end;
   a first flexible, dielectric tubular member coaxially surrounding the conductor coil for a longitudinal length;
   a first electrode coil coaxially surrounding the first tubular member for a longitudinal length less than the longitudinal length of the first tubular member and electrically connected to a second electrical connector located at the proximal end;
   a second flexible, dielectric tubular member coaxially surrounding the longitudinal length of the first electrode coil;
   a second electrode coil coaxially surrounding the conductor coil and having a proximal end located beyond the longitudinal length of the first electrode coil; and
   means for electrically and mechanically bonding at least a coaxial portion of the conductor coil and the second electrode coil,
   such that the conductor coil and the second electrode coil are wound in the same direction.

8. The multiple electrode defibrillation catheter of claim 7 further comprising:
   a third flexible, dielectric tubular member coaxially surrounding a distal portion of the first electrode coil and a proximal portion of the second electrode coil and extending longitudinally therebetween.

9. The multiple electrode defibrillation catheter of claim 7 further comprising:
a tip secured to the distal end of the catheter and having a bore into which a distal end of the conductor coil and the second electrode coil are inserted.

10. The multiple electrode defibrillation catheter of claim 7 wherein the first and the second electrode coils each have a maximum diameter of less than 6 French.

11. The multiple electrode defibrillation catheter of claim 10 where the maximum diameter is less than 4 French.

12. The multiple electrode defibrillation catheter of claim 7 wherein at least one of the first and second electrode coils has a longitudinal length that is more than thirty times a maximum diameter of the electrode coil.

13. The multiple electrode defibrillation catheter of claim 7 wherein the conductor coil and the second electrode coil are mechanically and electrically bonded together at a distal end of each.

14. The multiple electrode defibrillation catheter of claim 7 further comprising a cylindrical metallic element coaxial to which at least a portion of the conductor coil and the second electrode coil are mechanically and electrically bonded.

15. A multiple electrode cardioversion defibrillation transvenous catheter for defibrillating a human heart,
a. first and a second electrical connector covered with a dielectric insulating material, except for the most proximal portions thereof;
b. a junction member, covered with a dielectric insulating material, and with a bifurcated proximal end and a distal end,
joined to the first and second electrical connectors at each of the proximal furcations of the junction member, thereby forming a continuous outer surface of insulating dielectric material impervious to penetration by body fluids;
c. a first dielectric flexible plastic tubular member, a second dielectric flexible plastic tubular member, a first flexible wound electrode coil longer than the first tubular member and a flexible wound conductor coil, the proximal end of the conductor coil coaxially disposed within the second tubular member, the second tubular member coaxially disposed within the first electrode coil, the proximal portion of the first electrode coil disposed within the first tubular member, the first tubular member joined to the distal end of the junction member, thereby forming a continuous outer surface of insulating dielectric material, impervious to penetration to body fluids, the proximal end of the first electrode coil in electrical communication with the distal end of the first electrical connector within the junction member and the proximal end of the conductor coil in electrical communication with the distal end of the second electrical connector within the junction member, the second tubular member extending the length of the conductor coil, the first electrode coil extending past the distal end of the first tubular member, thereby becoming exposed;
d. a third dielectric flexible tubular member with a proximal flared end and a distal flared end,
the exposed distal end of the first electrode coil residing within the proximal flared end of the third tubular member, the conductor coil and second tubular member coaxially disposed within the portion of the third tubular member distal to the proximal flared end and distal to the distal end of the first electrode coil;
e. a second flexible wound electrode coil and a tined metal catheter tip,
the second electrode coil coaxially disposed around the second tubular member, the second tubular member coaxially disposed around the conductor coil, the proximal end of the second electrode coil disposed within the distal flared end of the third tubular member, the distal end of the second electrode coil disposed within the metal catheter tip, at least one of the electrode coils with an exposed length of at least about 30 times the maximum electrode diameter; and
f. means for rigidly and electrically bonding the distal end of the second electrode coil to the conductor coil, the second electrode coil coiled in the same direction as the conductor coil, the second electrode coil thereby being in electrical communication with the second electrical connector.

16. The catheter of claim 15, in which at least one electrode coil has a maximum diameter of less than 6 French and a length of at least 30 times the maximum electrode coil diameter.

17. A method of constructing a multiple electrode cardioversion defibrillation transvenous catheter for defibrillating a human heart, the method comprising the steps of:
a. providing a first and a second electrical connector covered with a dielectric insulating material, except for the most proximal portions thereof;
b. joining the first and second electrical connectors using a junction member, covered with a dielectric insulating material, and having a bifurcated proximal end and a distal end, thereby forming a continuous outer surface of insulating dielectric material impervious to penetration by body fluids;
c. providing a first dielectric flexible plastic tubular member, a second dielectric flexible plastic tubular member, a first flexible wound electrode coil longer than the first tubular member and a flexible wound conductor coil, the proximal end of the conductor coil being coaxially disposed within the second tubular member, the second tubular member being coaxially disposed within the first electrode coil, the proximal portion of the first electrode coil disposed within the first tubular member, the first tubular member joined to the distal end of the junction member, thereby forming a continuous outer surface of insulating dielectric material, impervious to penetration to body fluids, the proximal end of the first electrode coil in electrical communication with the distal end of the first electrical connector within the junction member and the proximal end of the conductor coil in electrical communication with the distal end of the second electrical connector within the junction member, the second tubular member extending the length of the conductor coil, the first electrode coil extending past the distal end of the first tubular member, thereby becoming exposed;
d. providing a third dielectric flexible tubular member with a proximal flared end and a distal flared end, the exposed distal end of the first electrode coil residing within the proximal flared end of the third tubular member, the conductor coil and second tubular member being coaxially disposed within the portion of the third tubular member distal to the proximal flared end and distal to the distal end of the first electrode coil;
e. providing a second flexible wound electrode coil and a tined metal catheter tip, the second electrode coil being coaxially disposed around the second tubular member, the second tubular member being coaxially disposed around the conductor coil, the proximal end of the second electrode coil disposed within the distal flared end of the third tubular member, the distal end of the second electrode coil disposed within the metal catheter tip, at least one of the electrode coils with an exposed length of at least about 30 times the maximum electrode diameter; and f. rigidly and electrically bonding the distal end of the second electrode coil to the conductor coil, the second electrode coil coiled in the same direction as the conductor coil, the second electrode coil thereby being in electrical communication with the second electrical connector.

18. The method of claim 17 in which step f is accomplished by laser welding, resistance welding or crimping.

19. The method of claim 17 in which step f is accomplished by laser welding a metallic pin to the distal end of the second electrode coil and the conductor coil.

20. The method of claim 17 in which step f is accomplished by resistance welding a metallic pin to the distal end of the second electrode coil and the conductor coil.

21. The method of claim 17 in which step f is accomplished by crimping a metallic pin to the distal end of the second electrode coil and the conductor coil.

22. The method of claim 17 in which step f is accomplished by laser welding a metallic tube to the distal end of the second electrode coil and the conductor coil.

23. The method of claim 17 in which step f is accomplished by resistance welding a metallic tube to the distal end of the second electrode coil and the conductor coil.

24. The method of claim 17 in which step f is accomplished by crimping a metallic tube to the distal end of the second electrode coil and the conductor coil.

25. The method of claim 17 in which step f is accomplished by laser welding a metallic pin and a metallic tube to the distal end of the second electrode coil and the conductor coil.

26. The method of claim 17 in which step f is accomplished by resistance welding a metallic pin and a metallic tube to the distal end of the second electrode coil and the conductor coil.

27. The method of claim 17 in which step f is accomplished by crimping a metallic pin and a metallic tube to the distal end of the second electrode and the conductor coil.

\* \* \* \* \*